United States Patent [19]

Fellows

[11] 4,122,192
[45] Oct. 24, 1978

[54] DISINFECTANT AND STERILIZING PREPARATIONS

[76] Inventor: Adrian Neville Fellows, 48 Bury New Rd., Ramsbottom, Bury, Lancashire, England

[21] Appl. No.: 790,981

[22] Filed: Apr. 26, 1977

[30] Foreign Application Priority Data

Apr. 26, 1976 [GB] United Kingdom ............... 16887/76
Jan. 17, 1977 [GB] United Kingdom ................. 1747/77

[51] Int. Cl.$^2$ .............................................. A01N 9/24
[52] U.S. Cl. ...................................... 424/333; 424/80
[58] Field of Search ................................. 424/333, 80

[56] References Cited

U.S. PATENT DOCUMENTS

| 3,016,328 | 1/1962 | Pepper et al. | 424/333 |
| 3,282,775 | 11/1966 | Stonehill | 424/333 |
| 3,697,222 | 10/1972 | Sierra | 424/333 |
| 3,700,611 | 10/1972 | Nickerson et al. | 260/17 R |
| 3,968,250 | 7/1976 | Boucher | 424/333 |

FOREIGN PATENT DOCUMENTS

| 1,006,202 | 11/1957 | Fed. Rep. of Germany | 424/333 |
| 765,696 | 1/1957 | United Kingdom | 424/333 |

OTHER PUBLICATIONS

Chem. Abst. 83 98,489(c) (1975) – Miki et al. "Hot water-dispersable P.V.A. powder".

Primary Examiner—Albert T. Meyers
Assistant Examiner—D. W. Robinson
Attorney, Agent, or Firm—Haight & Huard

[57] ABSTRACT

A solid composition for making up a disinfectant or sterilizing preparation, which comprises a disinfecting or sterilizing amount of saturated dialdehyde having from 2 to 6 carbon atoms absorbed and/or adsorbed on an inorganic or organic particulate carrier material and, in some cases, an alkalinating agent.

57 Claims, No Drawings

DISINFECTANT AND STERILIZING PREPARATIONS

This invention relates to disinfectant and sterilizing preparations.

For many years chemicals have been used for killing or inhibiting the growth of micro-organisms. None of the chemicals in use or proposed, however, is completely satisfactory: many chemicals do not have a sufficiently strong or extensive activity, while those chemicals that have the widest spectrum of activity against different kinds and forms of micro-organisms have undesirable properties that limit their use, for example, the cresols, the phenols and formaldehyde all have highly objectionable odours and are strong irritants.

A relatively recent addition to the broad spectrum microbiocides is glutaraldehyde (1,5-pentanedial). This compound has a number of advantages over other broad spectrum microbiocides eg. greater physiological tolerability, but has the drawback of lack of stability in solution at the alkaline pH's at which it is biologically active at ambient temperatures: under such conditions, glutaraldehyde polymerises extremely readily. Its use has, been limited, therefor, to those situations where it is practicable to prepare a buffered solution of appropriate pH before use. The preparation of such solutions has been facilitated by the provision of a solution of glutaraldehyde at a pH at which polymerisation occurs less readily but at which the biological activity is much reduced together with a sachet containing an appropriate amount of an alkaline buffer, the contents of the sachet being mixed with the glutaraldehyde solution immediately prior to use. The main disadvantages of this arrangement are the cost of transporting the large amounts of the dialdehyde solution, and lack of flexibility in making up solutions of different volumes.

It has been proposed to provide a dry dialdehyde preparation by spray drying the dialdehyde in the presence of an acid salt of an inorganic, sulphur-containing acid. The resulting product is the adduct of the dialdehyde and the acid. This, too, is not satisfactory, however, because the adduct does not dissociate sufficiently readily, and even when it does dissociate, the bisulphite released renders the dialdehyde biologically inactive.

The present invention provides a solid composition suitable for use in making up a microbiocidal solution, or dispersion, which comprises
(a) a saturated dialdehyde having from 2 to 6 carbon atoms absorbed and/or adsorbed on an inorganic or organic particulate carrier material or on a mixture of two or more such carrier materials, and
(b) an alkalinating agent or agent capable of yielding an alkalinating agent on admixture with a solvent for the dialdehyde, said carrier material being capable of adsorbing and/or absorbing the dialdehyde to give a substantially dry free-flowing particulate material that on subsequent admixture with a solvent for the dialdehyde substantially releases the dialdehyde.

The aldehyde is, for example, malonaldehyde, succinaldehyde, adipaldehyde, glyoxal, but is preferably glutaraldehyde.

The carrier material or matrix may be an organic substance, for example, a natural or synthetic polysaccharide, for example, a starch, for example, maize starch, or a cellulose derivative, for example, methylcellulose or carboxymethylcellulose, but in general inorganic carriers are preferred. The preferred inorganic carriers or matrices fall into two categories, which overlap to a certain extent:
(i) the anhydrous salts and those salts possessing higher or lower levels of hydration and that are capable of taking up water, and (ii) the adsorbent and/or absorbent minerals both natural and synthetic.

It will be appreciated that any salt used must not interfere with the achievement of the desired pH on addition of a solvent or dispersing agent, nor must the salt be so strongly alkaline that the dialdehyde is especially predisposed to polymerise either in the solid state or on solution. The preferred salts are sodium sulphate and potassium sulphate; anhydrous sodium sulphate being particularly preferred on account of the high degree of hydration possible. These salts also have the advantage of being water soluble, so provided that all the other components used are water soluble, the solid composition of the invention is water soluble. This is advantageous with regard to subsequent use of the biocidal preparation, particularly if it is to be sprayed.

A preferred solid composition of the invention comprises glutaraldehyde adsorbed and/or absorbed on sodium sulphate, and sodium bicarbonate microencapsulated in polyvinylalcohol or polyvinylpyrrolidone. This composition is water soluble.

The preferred mineral carriers or matrices are various forms of silica, for example, diatomaceous earth, keiselguhr, fumed silica, precipitated silica, hectorite, bentonite, attapulgite, the montmorillonite clays, fullers' earth, and sol- and gel-forming grades of synthetic hectorite, for example, Laponite XLG and XLS, of which diatomaceous earth, fumed silica, precipitated silica, and sol- and gel-forming grades of synthetic hectorite are particularly preferred. Other minerals which fulfil the above requirements may also be used, for example, talc, chalk, kaolin, china clay, and whitings.

In some cases the carrier itself may function as the alkalinating agent and/or may incorporate the alkalinating agent. An alkalinating agent present in this form is called herein an internal alkalinating agent. The amount of akalinating agent present in such a form may be sufficient to achieve the desired pH on solution or dispersion of the composition, or it may be necessary to add some further, external alkalinating agent. Examples of carriers which fall into this category are the synthetic hectorites which comprise a peptiser, especially tetrasodium pyrophosphate for example, Laponite XLS.

When the solid composition is brought into liquid or gel form for use, the preparation must be alkaline at ambient temperature, ie. it must have a pH of more than 7, to have biocidal activity. The pH is preferably at least 7.4, and it is also preferable that the pH does not exceed 9.5. The alkalinating agnt therefore, should be one chosen and used in an amount suitable for producing such pH values, and it is advantageous to use an alkalinating agent that has buffering properties. An inert organic base is suitable, but an inert inorganic base is preferred. The preferred alkalinating agents are the alkali metal carbonates, bicarbonates and phosphates either alone or in any mixture of two or more thereof. Sodium bicarbonate and tetrasodium pyrophosphate are particularly advantageous.

In a preferred form of the composition of the invention, the alkalinating agent is encapsulated or coated, especially microencapsulated. The material to be used to encapsulate the alkalinating agent must be capable of releasing the alkalinating agent in the solvent for the dialdehyde, and is preferably soluble therein. The medium most generally used to prepare a liquid preparation is water, which is a solvent for the dialdehydes in question, so the encapsulating or coating material is preferably soluble in water, including hot water. Suitable encapsulating and coating agents include, but are not limited to, gelatin and cross-linked gelatin, emulsified fats, hardened tallow, calcium alginate containing sodium ions, and preferably polyvinyl pyrrolidone and polyvinyl alcohol.

It will be understood that the amount of the various components in the composition will depend, inter alia, on the strength of the dialdehyde solution to be produced, the relative strengths of the dialdehyde and the alkalinating agent, and the adsorptivity and/or absorptivity of the carrier material or mixture of carrier materials used. Broad limits, given as a general indication only, are as follows, the values being percentages by weight calculated on the weight of the composition:

|  | useful | preferred |
|---|---|---|
| Carrier material, salt/mineral | 5 – 75% | 50 – 70% |
| Carrier material, salt | 70 – 90% | 65 – 75% |
| Carrier material, mineral | 0.5 – 50% | 30 – 50% |
| Dialdehyde (active) | 5 – 30% | 5 – 25% |
| Encapsulated buffer where appropriate | 0.5 – 10% | 2 – 5% |

The compositions of the invention may comprise one or more further substances, for example, selected from anionic, cationic nonionic and amphoteric surfactants, especially sodium lauryl sulphate, corrosion inhibitors, defoaming agents, chelating agents, dyes and perfumes, and other biocidal substances, for example, insecticides, for example, pyrethrum and derivatives thereof, DDT, dialdrin and other chlorinated hydrocarbons, γ-BHC, and organophosphorus insecticides, nematocides, and molluscicides, for example, metaldehyde. Surfactants are particularly useful because when the composition is made up in liquid form and applied, they assist in wetting any microorganisms with which the dialdehyde comes into contact, which facilitates the initial contact. Surfactants also aid penetration of the dialdehyde to the microorganism if it is protected by detritus or other material. It will be appreciated that any material incorporated in the composition should be inert. It must be compatible with the dialdehyde and should not adversely affect the performance, storage characteristics or general acceptability of the composition to a significant extent. Accordingly, hygroscopic materials and those capable of reacting with the dialdehyde are undesirable.

The compositions of the invention are substantially dry, particulate or pulverulent materials eg. powders or granules. They are preferably free-flowing. It is advantageous to dispense the composition in unit dose form, for example, in sachets or as tablets or capsules. A unit dose comprises, for example, from 0.05 to 25 g of active aldehyde, together with an appropriate amount of alkalinating agent, for example, from 0.1 to 50 g of Laponite XLS, or 0.0075 to 15 g of bicarbonate.

The compositions are prepared by admixing the dialdehyde and the carrier or matrix material, and then where appropriate admixing the alkalinating agent.

The invention also provides a solid composition comprising a saturated dialdehyde having from 2 to 6 carbon atoms adsorbed and/or absorbed on a carrier material (a) as defined above or on a mixture of two or more such carrier materials, especially those capable of functioning as the alkalinating agent and/or incorporating the alkalinating agent.

The invention further provides a two-pack system which comprises a pack comprising a dialdehyde adsorbed and/or absorbed on a carrier material according to the present invention together with a pack comprising one or more alkalinating agents. The pack preferably comprises instructions indicating the amounts to be used of the two components and of the solvent or dispersing agent. Preferably both the dialdehyde component and the alkalinating agent are in unit dose form. The discussion above regarding the amounts of these components in unit dose form is also applicable in this context.

The dialdehyde component and the alkalinating agent component may also be present in solid particulate form in a two component aerosol.

Although in some cases it is possible to use the solid dialdehyde/alkalinating agent composition itself, it is generally necessary to bring it into a liquid or gel form for use as a biocide. The solid dialdehyde/alkalinating agent composition of the invention may be admixed with a dialdehyde solvent to give a solution, if all the other components are also soluble in the medium, or a dispersion, if they are not also soluble. Water is the solvent generally used, but under some circumstances another polar solvent eg. an aqueous alkanol may be preferred. It is also possible to prepare a stable fluid dispersion in an appropriate medium. It will be appreciated that in some cases for ease of application it is preferable to have a solution or a homogeneous dispersion. This is especially important if the biocide is to be sprayed.

An alternative form of biocidal preparation is a gel, particularly a thixotropic gel, which has all the advantages known for preparations of this type. Some of the inorganic carriers mentioned above, for example, fumed silica and Laponite XGL and XLS, are thixotropic gel-forming agents.

The dialdehyde preparation of the invention and the two-pack system of the invention give liquid and gel biocidal preparations as described above. In the former case, it is necessary to admix an alkalinating agent as well as the solvent or dispersing agent.

The pH of the biocidal preparations should not be less than 7, preferably not less than 7.4, and preferably should not exceed 9.5.

All the liquid and gel biocidal preparations obtained from the compositions and two-part systems of the invention are themselves part of the invention.

The dialdehydes used in the invention and especially glutaraldehyde are capable of killing bacteria and fungi, and even viruses and bacterial spores. It is believed that they may also have molluscicidal activity. In general, liquid preparations and gels comprising from 0.05 to 0.25% of active dialdehyde are suitable for disinfection involving killing fungi and vegetative forms of bacteria, but higher concentrations, generally up to 0.5% may be used, for example, in more dirty situations. If a sterilizing preparation capable of killing viruses and spores is desired, the concentration of active dialdehyde should be about 2 to 2.5%, but again, higher concentrations, for example, up to 10%, may be used under certain circumstances.

The biocidal preparations of the invention, both the liquids and the gels, and even the compositions themselves in some cases, may be used to disinfect or sterilise articles and surfaces, for example, in domestic, industrial, medical, agricultural and horticultural situations. In the home, the preparations may be used as disinfectants in the usual manner, for example, to disinfect floors, walls and lavatories. Solutions and gels containing from 0.05 to 0.25% active aldehyde are generally used for this purpose, but more concentrated solutions, for example, up to 0.5% may be used, for example, for disinfecting lavatory bowls. In the medical field in the broadest sense, that is to say, in human and veterinary medicine and surgery and in dentistry, preparations containing 0.05 to 0.25% of active aldehyde, may be used to disinfect walls, floors and non-surgical or medical apparatus eg. beds and bedpans. As indicates for domestic use, the concentration may be higher eg. up to 0.5%, for example, for disinfecting bedpans. More concentrated solutions, for example, up to 2.5%, generally about 2% may be used to sterilize instruments and apparatus. Even higher concentrations, may be used if necessary. Disinfection and sterilization of walls and floors is particularly important in the food, dairy, brewing and pharmaceutical industries, as is disinfection of apparatus, for example, manufacturing vessels, storage vessels and fermentation vessels, filling and packaging lines, and milking machines, used in those industries. Generally 0.05 to 0.25% solutions are used, but more concentrated solutions for example, containing 0.5% or more active aleehyde may be used if necessary.

The biocidal preparations of the invention have numerous applications in agriculture and horticulture, for example, they may be applied to seeds, soil, living crops, for example, cereals, brassicas, legumes, and root crops, and to harvested crops to prevent and/or combat infection by bacteria, fungi or viruses. Fruit and vegetables of all kinds are susceptible to deterioration caused by micro-organisms, soft fruit being particularly susceptible. For the treatment of living crops it is advantageous to incorporate an insecticide in the preparation.

Another aspect of the use of the solutions in agriculture is in animal health, particularly in situations where animals are reared intensively, especially in poultry rearing. In the latter case, the dialdehyde may be used topically on the poultry, and is particularly effective when sprayed into the broiler house. A solution containing 0.05 to 0.5%, generally 0.05 to 0.25% active aldehyde is suitable in most circumstances. It is also useful as a medium in which eggs are washed, again generally at a concentration of 0.05 to 0.5%, usually to 0.25% active aldehyde, as such disinfectant washing reduces the risk of infection of the egg with bacteria, particularly salmonellae. The biocidal preparations are also useful as disinfectants of farm buildings and apparatus, for example, milking parlours, pens, stalls and stables, and is particularly useful for the widespread disinfection required in outbreaks of virus diseases, for example, foot-and-mouth disease, swine vesicular disease and Newcastle disease (fowl pest). As indicated above, preparations containing 0.05 to 0.25% active aldehyde are suitable for general disinfection. For more dirty situations, up to 0.5% is generally used. It is is desired to kill viruses eg. in outbreaks of viral diseases, the highest concentrations mentioned are generally used, that is to say, up to 2.5%, generally about 2% active aldehyde.

The biocidal preparations may be used topically in animal health care, as indicated above, and may also be used topically in the treatment of bacterial, fungal and viral infections of man. The preparation may be a solution of dispersion, for example, for treating athletes' foot, but in some circumstances it is advantageous to use a gel, which can be applied easily to the desired area and to that area only, for example, in the treatment of warts and ringworm. For treatment of fungal infections, for example, athletes' foot, preparations comprising 1 to 2% active aldehyde may be used, whereas preparations comprising 2 to 10% of active aldehyde are preferred for the topical treatment of viral infections, for example, warts and verrucas.

It is to be understood that the invention includes the methods of disinfection, sterilization and treatment described above.

The concentration of the dialdehyde, the nature of the carrier or matrix and encapsulating material and the additives, if any, are chosen having regard to the use to be made of the resulting solution, for example, it is clearly undesirable to use a carrier that forms a precipitate or an encapsulating agent that forms a gummy precipitate if the solution is to be applied by spraying. The provision of the composition in unit dosage form assists the selection and preparation of a solution suitable for a particular task.

Without further elaboration, it is believed that one skilled in the art can, using the preceding description, utilize the present invention to its fullest extent. The following preferred and specified embodiments are, therefore, to be considered as merely illustrative and not limitative of the remainder of the disclosure in any way whatsoever.

In the following Examples, temperatures are expressed in degrees Celsius and parts and percentages are by weight unless specified otherwise. Mixed aerobic spores are, unless specified otherwise, obtained from mixed vegetable detritus from waste trolleys at Mars Mill, Rochdale, Lancashire, England, and B. subtilis, unless otherwise indicated, is strain NCTC 10452.

EXAMPLE 1

70 g of anhydrous sodium sulphate were mixed with 5 g of fumed silica (Cab-O-Sil M-5) and 20 g of a 50% solution of glutaraldehyde was sprayed on to this mixture with continuous agitation. When three components were mixed intimately, 2 g of sodium lauryl sulphate were added and mixed, and then 3 g of an 80:20 (w/w) sodium bicarbonate: polyvinyl pyrrolidone encapsulated buffer. The product was 100 g of a dry, free-flowing substantially white powder.

EXAMPLE 2

The composition described in Example 1 was prepared by adding the anhydrous sodium sulphate to the aqueous glutaraldehyde and then mixing in the fumed silica. The resultant powder was then mixed with the sodium lauryl sulphate and finally the encapsulated buffer.

EXAMPLE 3

The composition described in Example 1 was prepared by mixing the fumed silica with the aqueous glutaraldehyde and then adding the anhydrous sodium sulphate. The resultant powder was then mixed with the sodium lauryl sulphate and finally the encapsulated buffer.

EXAMPLES 4 TO 6

The compositions described in Examples 1 to 3 were prepared but with the omission of the microencapsulated buffer, which is added at the dissolution stage prior to use.

EXAMPLE 7

8 parts by weight of a 50% aqueous glutardaldehyde solution were stirred into 10 parts by weight of Laponite XLS. The product was a substantially white, dry, free-flowing powder.

EXAMPLE 8

The composition described in Example 7 was prepared and with it was mixed 0.5 parts by weight of sodium lauryl sulphate. The product was as described in Example 7.

EXAMPLES 9 TO 23

Compositions were prepared as described in Example 1 but having the following formulations, the values being parts by weight. The parts by weight of the aldehyde are those contained in a 50% aqueous solution thereof.

TABLE I

| Example | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|
| Glutardaldehyde | 5 | 5 | 10 | 10 | 10 | 10 | 10 | 20 | 20 | 20 | 20 | 20 | 20 | 33 | — |
| Glyoxal | — | — | — | — | — | — | — | — | — | — | — | — | — | — | 10 |
| Cab-O-Sil | — | — | 3 | — | — | — | — | — | 5 | 7 | — | — | — | 24 | 5 |
| Laponite XLS | — | — | — | — | — | 7 | — | — | — | — | 24 | 24 | 50 | — | — |
| Laponite XLG | — | — | — | — | — | — | 7 | — | — | — | — | — | — | — | — |
| Diatomaceous earth | — | — | — | — | 5 | — | — | 5 | — | — | — | — | — | — | — |
| Na$_2$SO$_4$ | 75 | 70 | 72 | 75 | 70 | 70 | 70 | 70 | 70 | — | 35 | 30 | — | — | 65 |
| K$_2$SO$_4$ | — | 5 | — | — | — | — | — | — | — | — | — | — | — | — | — |
| PVP/NaHCO$_3$ | 3 | 3 | 3 | 3 | 3 | 3 | 3 | 3 | 3 | 2.9 | 6 | 6 | 10 | 10 | 3 |
| Na lauryl sulphate | 2 | 2 | 2 | — | 2 | — | 2 | 2 | 2 | 2 | 2 | — | — | — | 2 |

All the products were substantially white, dry, free-flowing powders.

EXAMPLES 24 TO 38

Compositions were prepared having the formulations given for Examples 9 to 23 except that polyvinyl alcohol microencapsulated sodium bicarbonate was substituted for polyvinylpyrrolidone microencapsulated sodium bicarbonate. All the products were substantially white, dry, free-flowing powders.

EXAMPLES 39 TO 49

These Examples illustrate the biocidal activity of preparations of the invention. The compositions referred to in these Examples correspond to the above formulations as follows:

| TOPSPEC | TME 10 PB | Example 17 |
|---|---|---|
| | TME 10 | Example 32 |
| | TME 5 PB | Example 9 |
| | TME 5 | Example 24 |
| | TME 2 | Example 22 |

EXAMPLE 39

TABLE II

| | BACTERICIDAL ACTIVITY TOSPEC TME 10 PB. |
|---|---|
| Test Procedure | TOSPEC TME 10 PB in tap water. |
| Contact Time | 2 – 30 mins |
| Temperature | 20° |
| Test organism | Group II Micrococcus |
| Inactivator | Double Strength Nutrient Broth + 3% Tween 80 |
| Recovery Medium | Nutrient Agar + 3% Tween 80 |
| Incubation | 72 hours at 37° |

RESULTS

| Contact time (minutes) | SURVIVORS PER ML | | | |
|---|---|---|---|---|
| | % Active Conc'n TME 10 | 0.25% 1:40 | 0.1% 1:100 | 0.05% 1:200 | Con. |
| 0 | | $3 \times 10^6$ | $3 \times 10^6$ | $3 \times 10^6$ | $3 \times 10^6$ |
| 2 | | 0 | 0 | 24,500 | $3 \times 10^6$ |
| 10 | | 0 | 0 | 0 | $3 \times 10^6$ |
| 30 | | 0 | 0 | 0 | $3 \times 10^6$ |

Protocol
1 ml of nutrient broth containing $3 \times 10^8$ organisms per ml added to 99 ml of test solution.
Contact time allowed, then removed for 1 : 100 serial dilution in inactivator solution.
Transfer 1 ml of final dilution to recovery medium.
Results mean of triplicate.

EXAMPLE 40

| | SPORICIDAL ACTIVITY OF TOSPEC UNDER HEAVY CONTAMINATION |
|---|---|
| Test Materials | Tospec TME 10 and Tospec TME 5 |
| Concentration | 2% active |
| Contact time | 2 hours and 3 hours |
| Temperature | 20° C |
| Test Organism | mixed Aerobic spores |
| Contamination. | 25g of mixed vegetable Detritus per 100g of test solution. |
| Inactivator | Double strength Letheen Broth |
| Recovery medium | Nutrient Agar + 3% Tween 80 |
| Challenge | spores in above contamination |
| Incubation | 72 hours at 35° C |
| Control | (a) Domestos 1% active chlorine. |
| | (b) Glutaraldehyde (UC) 2% Active. |

| RESULTS | MEAN COUNT SURVIVORS PER ML | |
|---|---|---|
| Test material | 2 hours | 3 hours |
| Tospec TME 5 | 5,900 | <100 |
| Tospec TME 10 | 2.400 | <100 |
| Domestos | 116,000 | 84,000 |
| Glutaraldehyde | 69,000 | 27,000 |
| Water | 480,000 | 480,000 |

EXAMPLE 41

SPORICIDAL ACTIVITY TOSPEC TME 5 PB

| | (1) | (2) |
|---|---|---|
| Test Procedure | Capacity type | Sporicidal |
| Test Material | Tospec TME 5 PB | TME 5 PB |
| Contact time | 2 hours | |
| Temperature | Initial 55° C cooling to | 18° C at 2 hours |
| Test organism | Mixed Aerobic spores | B Subtilis |
| Organism origin | Mixed vegetable Detritus from waste trolleys at Mars Mill, Rochdale. | |
| Organic material | Spores held in 3g of above dust. | none |
| Inactivator | Double strength N B | Double strength N B |
| Recovery medium | Nutrient agar + 3% T 80 | Nutrient agar + 3% T 80 |
| Incubation | 72 hours at 35° C | 72 hours at 35° C |
| Active concentration | 2% | 2% |

RESULTS

| | Experiment 1 | | Experiment 2 | |
|---|---|---|---|---|
| Test Material and controls | Mean Count survivors ml | 1.F | Mean Count survivors ml | 1.F |
| Tospec TME 5 | 0 | $6.2 \times 10^4$ | 0 | $10^8$ |
| Tap Water | $6.2 \times 10^4$ | — | $10^8$ | — |
| FRESHLY PREPARED ALK GLUARALDEHYDE PROTOCOL | 0 | $6.2 \times 10^4$ | 1,100 | |

The innoculum was added to 100 ml of test solution (2% TOSPEC in Water). The suspension was periodically agitated. Triplicate 1 ml aliqots were removed and serially diluted 1:100 in inactivator 1 Triplicate 1 ml aliquots of the final dilution were added to 9ml of recovery medium for incubation.

EXAMPLE 42

BACTERICIDAL ACTIVITY OF TOSPEC TME 5 AND TME 10

| | |
|---|---|
| Test procedure | BDMA/BS 3286 (British Disinfectant Manufacturers Association/British Standard 3286) |
| Test Material | Tospec TME 5 and TME 10 |
| Concentration | 2%, 1%, 0.5%, 0.25% and 0.05% active |
| Contact time | 10 minutes |
| Temperature | 20° C |
| Test organism | as indicated |
| Culture origin | Leeds University collection |
| Inactivator | Double strength nutrient broth |
| Recovery medium | Nutrient broth and agar + 3% Tween 80 |
| Challenge | 1ml of overnight nutrient broth culture |
| Incubation | 72 hours at 35° C |

RESULTS

All the test organisms were killed by each of the test concentrations of both formulations within the contact time prescribed. Results table therefore applies to all test concentration for both TME 5 and TME 10

| | Solid recovery | Liquid recovery | Reinnoc of broth to check stasis. |
|---|---|---|---|
| S AUREUS | — — — | — — — | + + + |
| D PNEUMONIAE | — — — | + + + | |
| E. COLI | — — — | — — — | + + + |
| Ps AERUGINOSA | — — — | + + + | |
| P VULGARIS | — — — | — — — | + + + |
| K AEROGENES | — — — | — — — | + + + |
| S PARATYPHII | — — — | — — — | + + + |

− No Growth   + Growth

CONTROL COUNTS

| | |
|---|---|
| S AUREUS | $9.8 \times 10^7$/ml |
| E COLI | $3.0 \times 10^8$/ml |
| Ps AERUGINOSA | $5.8 \times 10^8$/ml |

NOTES
Tests were carried out in triplicate with 1:100 serial dilution in inactivator prior to transfer of final dilution to recovery medium.

EXAMPLE 43

SPORICIDAL ACTIVITY TOSPEC TME 10 PB

| | (1) | (2) |
|---|---|---|
| Test Procedure | Capacity type | Sporicidal |
| Test Material | Tospec TME 10 PB | Tospec TME 10 PB |
| Contact time | 2 hours | |
| Temperature | Initial 55° cooling to | 18° C at 2 hours |
| Test Organism | Mixed aerobic spores | B Subtilis |

SPORICIDAL ACTIVITY TOSPEC TME 10 PB

|  | (1) | (2) |
|---|---|---|
| Organism origin | Mixed vegetable detritus from was trolleys at Mars Mill, Rochdale. | |
| Organic material | spore held in 3g of above dust. | None |
| Inactivator | Double strength N B | Double strength N B |
| Recovery Medium | Nutrient agar + 3% T 80 | Nutrient agar + 3% T 80 |
| Incubation | 72 hours at 35° C | 72 hours at 35° C |
| Active concentration | 2% | 2% |

RESULTS

|  | Experiment 1 | | Experiment 2 | |
|---|---|---|---|---|
| Test material | Mean count survivors ml | I.F. | Mean count survivors ml | I.F. |
| Tospec TME 10 | 0 | $6.6 \times 10^4$ | 0 | $1 \times 10^8$ |
| Tap Water | $6.6 \times 10^4$ | — | $-10^8$ | — |
| 2% FRESHLY prepared alk Glutaraldehyde | 0 | $6.6 \times 10^4$ | 600 | |

Protocol

The innoculum was to 100 ml of test solution (2% TOSPEC in Tap Water). The suspension was periodically agitated. Triplicate 1 ml aliquots were removed and serially diluted 1:100 in activator. Triplicate 1 ml aliquots of the final dilution were added to 9 ml of recovery medium for incubation.

EXAMPLE 44

SPORIDICAL ACTIVITY TOSPEC TME 2

| Test Procedure | Capacity type. |
|---|---|
| Test Material | TOSPEC TME 2. |
| Contact time | <2 hours (Plating finished at 2 hours). |
| Temperature | Initial 55° C cooling to 17° C at 2 hours. |
| Test Organism | Mixed AEROBIC SPORES (largely B subtilis + cereus) |
| Organism Origin | Natural mixed vegetable, fibre + seed detritus obtained from cotton waste trolleys at Mars Mill, Courtaulds Ltd., Rochdale. |
| Organic Material | Test innoculum consisted of spores held in 3 g of above dust. |
| Inactivator | Nutrient broth + 3% Tween 80. |
| Recovery medium | Nutrient Agar (Difco) + 3% Tween 80. |
| Challenge | 3 g of spore containing dust/100 ml of test solution. |
| Incubation | 72 hours at 35° C. |
| Protocol | The spore containing dust was added to 100 ml of test material (2% active TOSPEC IN TAP WATER). The suspension was periodically agitated. Duplicate 1 ml aliquots were removed and serially diluted 1:100 in inactivator with agitation. Duplicate aliquots of the first dilution were added to 9 ml of recovery medium for incubation. |

RESULTS

| TEST MATERIAL + CONTROLS | MEAN COUNT SURVIVORS/ML | I.F. | NOTES |
|---|---|---|---|
| Tospec TME 2 | 0 | $5.8 \times 10^4$ | Sample prepared 43 days previously stored in open-cap container. |
| Water | 58,000 | — | |
| 2½% freshly prepared alkaline glutaraldehyde | 0 | $5.8 \times 10^4$ | |
| Blank | 0 | — | |

EXAMPLE 45

SPORICIDAL ACTIVITY TOSPEC TME - 2.

| Test Procedure | Capacity Type. |
|---|---|
| Test Material | TOSPEC TME - 2 |
| Concentrations | 2%, 1% and 0.5% active aldehyde. |
| Contact Time | 2 hours (plating finished at 2 hours) |
| Temperature | Initial 55° C cooling at 17° C at 2 hours. |
| Test Organism | B subtilis spores |
| Organism Origin | Difco Lab. (ATCC). |
| Organic Material | None. |
| Inactivator | Nutrient broth + 3% Tween 80. |
| Recovery Medium | Nutrient agar + 3% Tween 80 |
| Challenge | Suspension of spores in tap water, from ampoule. |
| Incubation | 72 hours at 35° C. |

Protocol

The spores were suspended in warm water 55° C, and aliquots of water were added to pre-weighed test material, (to make solution totally 100 g). Periodic agitation and recovery as in previous experiment.

| TEST MATERIAL & CONTROL | Mean Count Survivors/ML | I.F. |
|---|---|---|
| TME 2 (2%) | 0 | $6.35 \times 10^5$ |
| TME 2 (1%) | 315,000 | — |
| TME 2 (0.5%) | 602,500 | — |

SPORICIDAL ACTIVITY TOSPEC TME - 2.

| | | |
|---|---|---|
| Water | 635,000 | — |
| 2% ALK Glutaraldehyde | 5,350 | $1.30 \times 10^2$ |

Note:
B subtilis was chosen because in previous work by other workers it has proved particularly hardy with respect to glutaraldehyde, cf. U.S. Pat. No. 3,016,328.

EXAMPLE 46

SPORICIDAL ACTIVITY OF TOSPEC TME 2 UNDER CONDITIONS OF HEAVY CONTAMINATION

| | |
|---|---|
| Test Material | TOSPEC TME 2 |
| Concentration | 2% active aldehyde |
| Contact time | 2 hours and 3 hours. |
| Temperature | 20° C. |
| Test Organisms | Mixed aerobic spores. |
| Organic Material | 25 g mixed vegetable detritus/100 g of test solutions. |
| Inactivator | Nutrient broth + 3% Tween 80. |
| Recovery Medium | Nutrient agar (Difco) + 3% Tween 80. |
| Challenge | Spores contained in above organic matter. |
| Incubation | 72 hours at 35° C. |
| Control | (a) Water<br>(b) 1% active chlorine, hypochlorite detergent. |
| Protocol | Challenge was added to the test solutions (100 ml) with agitation. At the end of the contact time, duplicate aliquots (1 ml) were serially diluted 1:100 in inactivator solution. Duplicate 1 ml samples were then added to Nutrient agar plus 3% Tween 80. Plates were then incubated. |

Results

| Test Material | Mean Count 2 hours | Survivors ml 3 hours |
|---|---|---|
| TME 2 (2% active) | 6,300 | < 100 |
| Hypochlorite (1% active) | 68,000 | 55,000 |
| Water | 160,000 | 160,000 |

EXAMPLE 47

CONTACT TIME OF TOSPEC TME 2 AGAINST BACILLUS SUBTILIS SPORES

| | |
|---|---|
| Test Procedure | Sporicidal contact time. |
| Test material | TOSPEC TME 2 |
| Concentration | 2% active aldehyde. |
| Temperature | 20° C. |
| Test Organism | B subtilis spores. |
| Organism origin | NCTC 10452 |
| Organic material | none |
| Inactivator | Nutrient broth + 3% Tween 80 |
| Recovery Medium | Nutrient agar + 3% Tween 80 |
| Challenge | one ampoule of spore suspension containing $10^8$ spores/ml. |
| Incubation | 72 hours at 35° C. |
| Protocol | a solution of the test material was prepared in 100 ml of tap water. The contents of an ampoule of spore suspension (DIFCO) were aseptically transferred to a test solution. At each contact time duplicate aliquots were serially diluted 1:100 in inactivator solution. Duplicate 1 ml samples were then transferred to the recovery medium for incubation. |

Results

| Test Material | Contact time | Mean Count Survivors ml. |
|---|---|---|
| TME 2 | 0 mins | $10^8$ |
| " | 5 mins | 700,000 |
| " | 15 mins | 6,750 |
| " | 30 mins | 450 |
| " | 60 mins | 0 |

Bacillus subtilis was chosen because in previous work by other workers it has consistently proved to be the most resistant bacterial spore with respect to treatment by chemical agents especially glutaraldehyde.

EXAMPLE 48

BACTERICIDAL ACTIVITY TOSPEC TME 2

| | |
|---|---|
| Test Procedure | B.D.M.A./BS 3286 |
| Test Material | TOSPEC TME 2 2% active aldehyde. |
| Contact time | 2 minutes |
| Temperature | 20° C. |
| Test Organism | As indicated. |

-continued
BACTERICIDAL ACTIVITY TOSPEC TME 2

| | | | |
|---|---|---|---|
| Origin of Culture | Leeds University Collection. | | |
| Inactivator | Nutrient broth + 3% Tween 80 | | |
| Recovery Medium | Nutrient agar + 3% Tween 80. Double strength Letheen Broth | | |
| Challenge | 1 ML of nutrient broth culture incubated at 37° C for 24 hours | | |
| Incubation | 72 hours at 37° C. | | |
| RESULTS | SOLID RECOVERY | LIQ RECOVERY | REINNOC OF LIQ TO CHECK STASIS |
| S AUREUS | --- | --- | +++ |
| STR PYOGENES | --- | --- | +++ |
| D PNEUMONIAE | --- | --- | +++ |
| E COLI | --- | --- | +++ |
| Ps AERUGINOSA | --- | --- | +++ |
| Ps FLUORESCENS | --- | --- | +++ |
| P VULGARIS | --- | --- | +++ |
| K AEROGENES | --- | --- | +++ |
| B SUBTILIS | --- | --- | +++ |

—No growth    Growth +

CONTROL COUNTS

| | | |
|---|---|---|
| | S AUREUS | $6.5 \times 10^7$/ml |
| | E. COLI | $5.0 \times 10^7$/ml |
| | Ps AERUGINOSA | $1.2 \times 10^8$/ml |

METHOD 1 ml challenge to 9 ml TOSPEC TME 2. 2 minutes contact time withdrawal of 1 ml test solution and add to 9 ml inactivator 2 minutes, transfer 1 ml in triplicate to 9 ml solid and liquid recovery media.

NOTE:
Similar results were obtained using TOSPEC TME 2 at 1%, 0.5% and 0.05% active aldehyde.

EXAMPLE 49

Preparations TME 5 and TME 10 were tested for their germicidal and sporicidal properties in accordance with the official sporicidal test adopted by the Association of Official Agricultural Chemists (A.O.A.C. 1961).

Briefly, this test comprises exposing porcelain cylinders carrying bacteria or bacterial spores to the test solution for different periods of time at a temperature of 20° C. and then transferring the cylinders to a subculture medium known to support the growth of such micro-organisms. The cultures (including controls) are incubated at 37° C. for 1 week or 2 weeks as the case may be. If no growth is observed in the subculture media after the 2-week period the solution is considered bactericidal or sporicidal (as the case may be).

The spores against which the preparations were tested were NCTC strains of *Bacillus globigii, Bacillus subtilis, Clostridium tetani* and *Clostridium welchii*. Standard tests, known in the art, were conducted to rule out bacteriostasis or sporistasis.

Both preparations were found to kill *Bacillus globigii, Bacillus subtilis, Clostridium tetani* and *Clostridium welchii* organisms in a period of less than 3 hours.

The preceding Examples can be repeated with similar success by substituting a generically or specifically described composition and/or operating conditions of the invention for those used in the preceding Examples.

From the foregoing description, one skilled in the art can easily ascertain the essential characteristics of this invention and, without departing from the spirit and scope thereof, can make various changes and modifications of the invention to adapt it to various usages and conditions.

What I claim is:

1. A solid composition suitable for preparing a microbiocidal solution or dispersion, which comprises:
   (a) about 5-30% by weight of an active monomeric saturated dialdehyde having from 2 to 6 carbon atoms sorbed on at least one particulate carrier material, and
   (b) an effective amount of a dry alkalinating agent or an agent capable of yielding an alkalinating agent on admixture with a solvent for the dialdehyde, the carrier material being capable of sorbing the dialdehyde to give a substantially dry, free-flowing particulate material that on subsequent admixture with a solvent for the dialdehyde releases substantially all of the dialdehyde.

2. A composition according to claim 1, which comprises from 5 to 25% by weight, calculated on the composition, of the aldehyde.

3. A composition according to claim 1, wherein the aldehyde is glutaraldehyde.

4. A composition according to claim 1, wherein the aldehyde is malonaldehyde, succinaldehyde, adipaldehyde or glyoxal.

5. A composition according to claim 1, wherein the carrier material is a particulate polysaccharide or cellulose derivative.

6. A composition according to claim 1, wherein the carrier material is an inorganic substance.

7. A composition according to claim 6, wherein the carrier is sodium sulphate or potassium sulphate.

8. A composition according to claim 6, wherein the carrier is silica.

9. A compositon according to claim 8, wherein the carrier is diatomaceous earth or precipitated silica.

10. A composition according to claim 8, wherein the carrier is fumed silica or a sol- or gel-forming grade of synthetic hectorite.

11. A composition according to claim 10, wherein the carrier is a synthetic hectorite which further comprises a peptiser.

12. A composition according to claim 11, wherein the peptiser is tetrasodium pyrophosphate.

13. A composition according to claim 8, wherein the carrier is hectorite, bentonite, attapulgite, a montmorillonite clay or Fuller's earth.

14. A composition according to claim 6, wherein the carrier is talc, chalk, kaolin, china clay or whitings.

15. A composition according to claim 1, wherein the alkalinating agent is an alkali metal carbonate, bicarbonate or phosphate, or a mixture of two or more thereof.

16. A composition according to claim 15, wherein the alkalinating agent is sodium bicarbonate or tetrasodium pyrophosphate.

17. A composition according to claim 1, wherein the alkalinating agent is encapsulated or coated.

18. A composition according to claim 17, wherein the alkalinating agent is microencapsulated.

19. A composition according to claim 17, wherein the encapsulating or coating material is water-soluble.

20. A composition according to claim 19, wherein the encapsulating or coating material is selected from the group consisting of gelatin and cross-linked gelatin, emulsified fats, hardened tallow, calcium alginate containing sodium ions, polyvinyl pyrrolidone and polyvinyl alcohol.

21. A composition according to claim 1, wherein the carrier itself functions as or incorporates the alkalinating agent, and further alkalinating agent is present.

22. A composition according to claim 1, which also comprises an effective amount of one or more substances inert to the dialdehyde and selected from the group consisting of anionic, cationic, non-ionic and amphoteric surfactants, corrosion inhibitors, defoaming agents, chelating agents, dyes and perfumes, and other biocidal substances.

23. A solid composition suitable for preparing a microbiocidal solution, which comprises a microbiocidally effective amount of a monomeric saturated dialdehyde having from 2 to 6 carbon atoms sorbed on a particulate synthetic hectorite carrier material to give a substantially dry, free-flowing, particulate material capable of subsequently releasing substantially all of the dialdehyde on subsequent admixture with a solvent for the dialdehyde.

24. A composition according to claim 23, which comprises from 1 to 50% by weight, calculated on the composition, of the aldehyde.

25. A composition according to claim 23, which comprises from 1 to 30% by weight, calculated on the composition, of the aldehyde.

26. A composition according to claim 23, which comprises from 1 to 25% by weight, calculated on the composition, of the aldehyde.

27. A composition according to claim 23, wherein the carrier is a synthetic hectorite which comprises a peptiser.

28. A composition according to claim 27, wherein the peptiser is tetrasodium pyrophosphate.

29. A composition according to claim 23, wherein the carrier is sodium sulphate or potassium sulphate.

30. A composition according to claim 23, which also comprises an effective amount of one or more substances inert to the dialdehyde and selected from the group consisting of anionic, cationic, non-ionic and amphoteric surfactants, corrosion inhibitors, defoaming agents, chelating agents, dyes and perfumes, and other biocidal substances.

31. A composition according to claim 1, in unit dosage form, which comprises from 0.05 to 25 g of active aldehyde per unit dose.

32. A composition according to claim 31, which comprises from 0.05 to 25 g of active aldehyde and from 0.1 to 50 g of a sol- or gel-forming grade of synthetic hectorite per unit dose.

33. A composition according to claim 31, which comprises from 0.05 to 25 g of active aldehyde and from 0.0075 to 15 g of an alkali metal bicarbonate per unit dose.

34. A composition according to claim 23 comprising from 0.05 to 25 g of active aldehyde.

35. A gel biocidal preparation which comprises a composition according to claim 1 in admixture with a dialdehyde solvent, wherein the particulate carrier is an inorganic substance selected from the group consisting of diatomaceous earth, fumed silica, precipitated silica and sol- and gel-forming grades of synthetic hectorite.

36. A gel biocidal preparation which comprises a composition according to claim 23 and an alkalinating agent in admixture with a dialdehyde solvent.

37. A gel biocidal preparation which comprises a composition according to claim 27 in admixing with a dialdehyde solvent.

38. A preparation according to claim 35, wherein the dialdehyde solvent is water.

39. A preparation according to claim 35, which comprises up to 5% of active dialdehyde.

40. A preparation according to claim 39, which comprises up to 2% of active dialdehyde.

41. A preparation according to claim 40, which comprises up to 0.5% of active dialdehyde.

42. A preparation according to claim 41, which comprises from 0.05 to 0.25% of active dialdehyde.

43. A method of disinfecting or sterilizing a surface infected by micro-organisms or susceptible to infection by micro-organisms, which comprises applying to the surface a disinfecting or sterilizing amount of a preparation prepared by mixing the composition of claim 1 with a dialdehyde solvent.

44. A method as claimed in claim 43, wherein the surface is selected from the group consisting of floors, walls, working surfaces, lavatories, urinals and bed pans.

45. A method according to claim 43, wherein the surface is a surgical or medical instrument or device.

46. A method according to claim 43, wherein the surface is a dental instrument or device.

47. A method according to claim 43, wherein the surface is an apparatus utilized in the food, dairy, brewing or pharmaceutical industry.

48. A method according to claim 43, wherein the surface is soil.

49. A method according to claim 43, wherein the surface is a living crop.

50. A method according to claim 49, wherein the preparation also comprises an insecticide.

51. A method according to claim 43, wherein the surface is seeds or a harvested crop.

52. A method according to claim 43, wherein the surface is selected from the group consisting of milking parlours, stalls, pens, barns and stables.

53. A method according to claim 43, wherein the surface is a poultry house.

54. A method according to claim 43, wherein the surface is an egg.

55. A method according to claim 43, wherein the surface is the surface of an animal.

56. A method according to claim 55, wherein the animal is poultry.

57. A method according to claim 55, wherein the animal is a human being.

* * * * *